United States Patent
Tsunakawa et al.

(10) Patent No.: US 6,974,470 B2
(45) Date of Patent: Dec. 13, 2005

(54) HEAT-GENERATIVE, STEAM GENERATION SHEET FOR FACE

(75) Inventors: Satoshi Tsunakawa, Cincinnati, OH (US); Conni Weaver, Cincinnati, OH (US); Masataka Ishikawa, Tochigi (JP); Yoshiaki Kumamoto, Tochigi (JP); Takao Orii, Tokyo (JP); Haruyo Kojima, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/787,181

(22) Filed: Feb. 27, 2004

(65) Prior Publication Data

US 2005/0192653 A1   Sep. 1, 2005

(51) Int. Cl.[7] ............................................. A61F 7/00
(52) U.S. Cl. ...................... 607/109; 607/96; 607/108; 607/112
(58) Field of Search ............................. 607/108, 109, 607/112, 96

(56) References Cited

U.S. PATENT DOCUMENTS

| | | | |
|---|---|---|---|
| 4,205,685 A * | 6/1980 | Yoshida et al. ............... 607/96 |
| 4,238,524 A | 12/1980 | LaLiberte et al. | |
| 4,303,701 A | 12/1981 | Torgersen et al. | |
| 4,307,149 A | 12/1981 | Scott et al. | |
| 4,329,378 A | 5/1982 | Tarumi et al. | |
| 4,753,241 A * | 6/1988 | Brannigan et al. ........... 607/112 |
| 5,135,591 A | 8/1992 | Vockel, Jr. et al. | |
| 5,194,289 A | 3/1993 | Butland | |
| 5,279,058 A | 1/1994 | Kohn | |
| 5,421,869 A | 6/1995 | Gundjian et al. | |
| 5,516,362 A | 5/1996 | Gundjian et al. | |
| 5,599,578 A | 2/1997 | Butland | |
| 5,605,738 A | 2/1997 | McGinness et al. | |
| 5,811,152 A | 9/1998 | Cleary | |
| 5,938,693 A * | 8/1999 | Carminucci ................. 607/104 |
| 6,261,314 B1 * | 7/2001 | Rich ........................... 607/109 |
| 6,409,746 B1 * | 6/2002 | Igaki et al. ................. 607/109 |
| 6,436,128 B1 * | 8/2002 | Usui ............................ 607/96 |
| 6,629,964 B1 * | 10/2003 | Ono et al. ................... 604/304 |
| 6,823,860 B2 * | 11/2004 | Igaki et al. ............ 126/263.05 |
| 6,824,557 B2 * | 11/2004 | Tone et al. ................. 607/114 |
| 2004/0098072 A1 * | 5/2004 | Tone et al. ................... 607/96 |
| 2004/0138729 A1 * | 7/2004 | Ladmer ...................... 607/109 |

FOREIGN PATENT DOCUMENTS

JP   2000-236945   9/2000
WO   WO 03/103444   12/2003

OTHER PUBLICATIONS

Organic Products Company Brochure, 6 pages; Material Safety Data Sheets, 2 pages.

* cited by examiner

*Primary Examiner*—Henry M Johnson, III
(74) *Attorney, Agent, or Firm*—Oblon, Spivak, McClelland, Maier & Neustadt, P.C.

(57) ABSTRACT

A heat-generative, steam generation facial sheet that is planar and is adapted to cover a part or the whole of a wearer's face in intimate contact. It has a planar heat generator capable of generating steam upon contact with oxygen in such a manner that the skin surface temperature reaches 34° C. or higher within 120 seconds from the contact with air and the skin surface temperature is maintained at 34° C. or higher for at least 5 minutes.

13 Claims, 4 Drawing Sheets

HEAT-GENERATIVE, STEAM GENERATION SHEET FOR FACE

FIELD OF THE INVENTION

The present invention relates to a heat-generative, steam generation sheet for a face that is adapted to intimately cover a part or the whole of a wearer's face to apply steam to the covered site of the face.

BACKGROUND OF THE INVENTION

A steam generating tool having a cup-shaped steaming mask with an opening is known (see WO 03/103444). Facial skin is covered with the opening side of the mask, and steam is generated in the mask in this state. The steam generating tool opens pores to effectively cleanse the skin. In addition, a medicine or a perfume can be incorporated into steam. Inhalation of such steam moistens the mucous membrane of the throat and the nose and provides relaxation.

Apart from this device, a facial mask fabricated of a fiber capable of generating heat on contact with an aqueous liquid is known (see JP-A-2000-236945). In using the facial mask, skin lotion or a like skincare product is applied to the face beforehand, and the facial mask is then brought into contact with the skin thereby to generate heat. The publication states that skin warmed by the generated heat improves penetrability of the skin lotion, etc.

With the steam generating tool of WO 03/103444, steam can be applied to a desired part of the face simply by covering the skin with the open side of the mask. It is easy to cover a part of the face but not easy to cover the whole face with this steam generating tool because of its cup shape. When a user wants the pores to open all over the face at a time as in makeup removal, it is troublesome to achieve this with such steam generating tool.

Because the facial mask of JP-A-2000-236945 makes use of a hygroscopic exothermic reaction, the heat generation performance is correlated to the amount of water added. That is, heat generation requires the trouble of supplying water beforehand. Besides, in order to obtain desired heat generation performance, water must be supplied in an amount corresponding to the desired amount of heat to be generated. This makes it difficult to obtain stable heat generation performance in actual use.

Accordingly, an object of the present invention is to provide a heat-generative, steam generation sheet for a face that is free of the above-described problems associated with the conventional techniques.

SUMMARY OF THE INVENTION

The above object is accomplished by a heat-generative, steam generation sheet for face (facial sheet) which is planar and adapted to intimately cover a part or the whole of a wear's face, and has a planar heat generator capable of generating steam upon contact with oxygen. The heat-generative, steam generation facial sheet generates steam such that the skin surface temperature reaches 34° C. or higher within 120 seconds from contact with air and maintains a skin surface temperature at 34° C. or higher for at least 5 minutes.

BRIEF DESCRIPTION OF THE DRAWINGS

FIG. 4($a$) and FIG. 4($b$) schematically show a third embodiment of the heat-generative, steam generation facial sheet of the present invention (corresponding to FIG. 1).

DETAILED DESCRIPTION OF THE INVENTION

Figure 1:
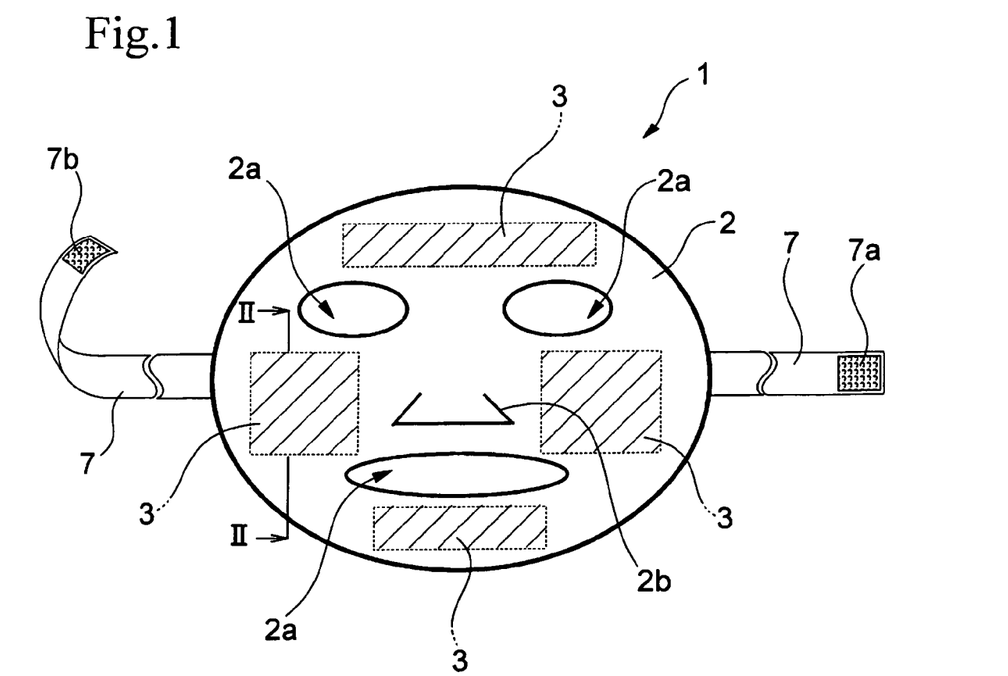
FIG. 1 schematically illustrates a steaming mask as an embodiment of the heat-generative, steam generation facial sheet of the present invention.
Figure 2:
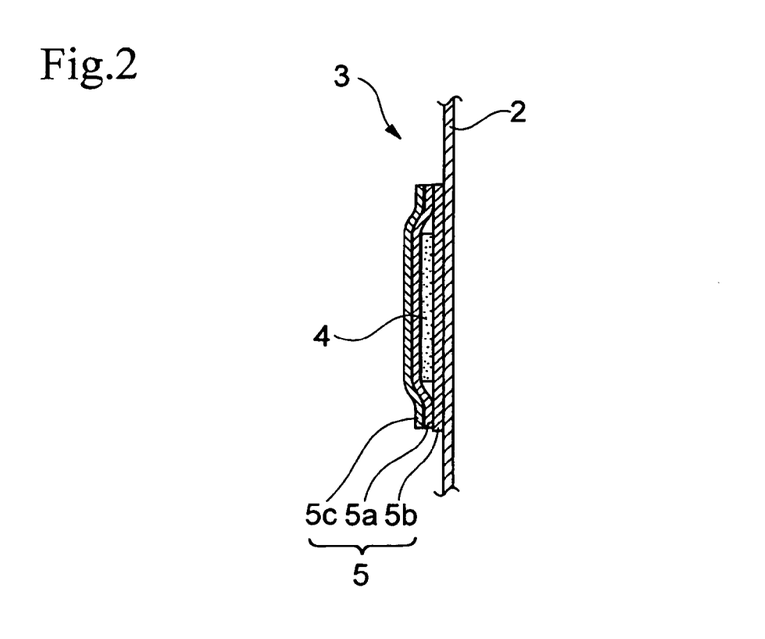
FIG. 2 is a cross-section taken along line II—II in FIG. 1.

The present invention will be described with respect to its preferred embodiments by referring to the accompanying drawings. FIG. 1 schematically shows a heat-generative steaming mask as an embodiment of the heat-generative, steam generation facial sheet of the present invention. A cross-section along line II—II of FIG. 1 is shown in FIG. 2. The steaming mask 1 shown in FIGS. 1 and 2 is planar and is composed of a mask body 2 made of a sheet material and planar steam generators 3.

The mask body 2 has the shape of a laterally elongated circle with an area sufficient to cover the whole face. The mask body 2 has the parts corresponding to the eyes and the mouth punched out to make openings 2$a$. The mask body 2 also has a slit 2$b$ at the part corresponding to the nose. The eyes of a wearer are thus exposed to the outside so that the wearer is allowed to do other work or move to another place while wearing the mask 1. With the mouth and the nostrils exposed, too, a wearer wearing the mask 1 feels no difficulty in breathing. With the nostrils exposed, a wearer hardly feels a temperature difference between inside and outside the mask.

The mask body 2 is composed of a single sheet material or a laminate of two or more sheet materials of the same or different materials. The mask body 2 shown in FIG. 2 is fabricated of a single sheet material. Nonwoven fabric that feels like cloth and can be economically manufactured is a preferred sheet material for fabricating the mask body 2. Nonwoven fabric made mainly of hydrophobic fiber is particularly preferred because sebum, which manly comprises oily components, exuded from pores by the action of steam is easily absorbed by the mask body 2.

Where the mask body 2 is made of nonwoven fabric, nonwoven fabrics produced by various techniques can be used, such as air-through nonwoven fabric, spun laced nonwoven fabric, spun bonded nonwoven fabric, melt blown nonwoven fabric, and needle punched nonwoven fabric. Preferred of them are air-through nonwoven fabric and spun laced nonwoven fabric in view of their good handling properties.

Fibers fabricating the nonwoven fabrics include hydrophobic fibers made of thermoplastic resins, such as polyolefin resins, e.g., polyethylene and polypropylene, polyester resins, e.g., polyethylene terephthalate, polyamide resins, and acrylic resins; and hydrophilic fibers, such as cellulosic fibers, such as natural cellulose fibers, e.g., cotton, regenerated cellulose fibers, e.g., rayon, and Tencel (registered trade mark), and hydrophobic fibers having been made hydrophilic with a hydrophilizing agent. Since sebum is composed mainly of oily components, nonwoven fabric made of hydrophobic fiber or a mixture of hydrophilic fiber and hydrophobic fiber is preferably used.

The nonwoven fabric preferably has a basis weight of 5 to 200 g/m², more preferably 10 to 100 g/m², in order to secure sufficient strength for the mask body 2 and not to impair its handling ability.

As shown in FIG. 2, the steam generator 3 is attached to the inner side of the mask body 2 that faces the skin. The steam generator 3 is attached to four sites of the mask body 2: the sites corresponding to the forehead, the cheeks, and the chin when the mask 1 is worn. These sites have particularly high sebum secretions. Each steam generator 3 has a rectangular shape.

The steam generator 3 is made of a rectangular, planar heat generator 4 hermetically sealed in a planar holder 5. The planar holder 5 has a moisture permeable film 5a on one side and a hardly moisture permeable film 5b on the other side. Both the moisture permeable film 5a and the substantially moisture impermeable film 5b extend outward from the perimeter of the planar heat generator 4 and bonded together at their extensions thereby to enclose the planar heat generator 4 therebetween hermetically. The planar holder 5 is attached with the side of its moisture permeable film 5a facing the inner side that faces the skin. To improve wearing comfort of the mask 1, a nonwoven fabric 5c that is a sheet material with good handling properties is provided on the outer side of the moisture permeable film 5a as shown in FIG. 2. Therefore, when using the mask 1, the nonwoven fabric 5c is brought into direct contact with the skin.

The planar holder 5 is attached to the skin facing side of the mask body 2 with the moisture permeable film 5a facing the skin, that is, with the substantially moisture impermeable film 5b in contact with the skin facing side of the mask body 2. The moisture permeable film 5a allows steam generated from the planar heat generator 4 to pass through, whereas the substantially moisture impermeable film 5b hardly allows steam to pass through. As a result, the steam is released outside from only one side of the holder 5, i.e., the side of the moisture permeable film 5a.

As previously stated, the mask body 2 has four steam generators 3 attached thereto. In other words, the mask body 2 has four planar heat generators 4. The total area of the planar heat generators 4 is preferably as close as possible to the area of the mask body 2 for greater steam generation. According to the present inventors' study, however, the following fact has been revealed. As long as the rate of steam generation as described infra is in a range of from 1 to 100 mg/cm²·10 min, a total area of the planar heat generators 4 of 25% or more, preferably 35% or more, of the area of the mask body 2a suffices for generating a sufficient amount of steam for producing intended effects.

As depicted in FIG. 1, the mask 1 has a pair of fastening straps 7 each extending laterally from the side edge of the mask body 2. The fastening straps 7 have attached to the respective free ends thereof an engaging member 7a and an engageable member 7b that is engageable with the engaging member 7a, respectively. In using the mask 1, the mask body 2 is applied to the face, and the fastening straps 7 are put around behind the head and fastened together via the engaging member 7a and the engageable member 7b to fix the mask 1 on the face. The fastening straps 7 may be of an extensible or non-extensible material. The fastening straps 7 are bonded to the mask body 2 of the mask 1 by heat sealing or with an adhesive.

Before use, the whole of the mask 1 of the present embodiment is packed in an oxygen barrier package (not shown) so as to keep the planar heat generators 4 away from contact with oxygen in air. Materials of such oxygen barrier package preferably include those having an oxygen transmission rate (ASTM D3985) of 10 cm³·mm/(m²·d·MPa) or lower, more preferably 2 cm³·mm/(m²·d·MPa) or lower, such as an ethylene-vinyl alcohol copolymer and polyacrylonitrile.

In putting on the mask 1, the package is opened to take out the mask 1, and the mask 1 is fixed to the face according to the procedure described above. On being removed from the package, the mask 1's planar heat generators 4 are exposed to oxygen in the air and generate heat, by which steam is generated. The generated steam is released outside from the side of the moisture permeable film 5a of the planar holder 5 and thereby applied to the skin. By the action of the steam, the skin temperature rises, and the pores open. The sebum in the pores becomes loose by the heat, and solidified sebum in the pores, such as a horny plug and a comedo, is released. After facial steaming for a prescribed time to make the sebum, etc. ready to be removed, the mask 1 is removed, and the sebum, etc. are washed away with a facial cleanser such as a scrub. Thereafter, if desired, the face can then be cooled with cool water to close the pores. Otherwise, the mask 1 may be used after makeup is removed with a facial cleanser or a makeup remover, and after the treatment with the mask 1, the face may be washed with a scrub or a cleanser to remove the sebum, etc. In this way, the dirt present in the pores, such as sebum, can be removed efficiently.

In order to efficiently remove the dirt in the pores such as sebum, the mask 1 of the present embodiment is designed to have a planar shape and to cover the face in intimate contact with the skin so that steam may be applied to the skin from close range. The time required for the skin to elevate its surface temperature to a prescribed one from the time when the mask 1 is taken out of its package and brought into contact with air, i.e., the rise time of the skin surface temperature is of significance. Too long a rise time means that the mask 1 should be worn for a long time, which is inconvenient for a user. From this viewpoint, the mask 1 is designed to generate steam of such amount and/or temperature so that the skin surface temperature reaches 34° C. or higher within 120 seconds, preferably within 60 seconds, from the contact with air and maintains the skin surface temperature at 34° C. or higher for at least 5 minutes.

Duration of steam generation as well as the rise time is important for efficient removal of the dirt in the pores such as sebum. With a short duration, the mask 1 can fail to sufficiently widen the pores for sufficient removal of the dirt such as sebum. From this standpoint, the mask 1 is designed to generate steam of such amount and/or temperature that the skin surface temperature may be maintained at 34° C. or higher for at least 5 minutes, preferably 10 minutes or longer. The recited temperature is sufficient for loosening sebum and making it easy to remove.

The rise time and duration can be measured as follows. Before measurement, a test subject spends enough time in an environment of 23° C. and 50% RH for conditioning her or his skin. A thermocouple is attached to the subject's face, and a mask is put thereon and heat is allowed to generate. Taking the readings of the thermocouple as the skin surface temperatures, the rise time and the duration are measured.

The amount of steam generated from the individual planar heat generators 4 is preferably 1 to 100 mg/cm²·10 min, more preferably 2 to 50 mg/cm²·10 min. The amount of steam generated can be measured as follows. A tester having a closed system with a volume, e.g., of 4.2 liters³ and an inner relative humidity adjusted to 1% or less is prepared. A mask 1 is put in the tester and heat is allowed to generate so as to release generated steam inside the tester while feeding dry air into the closed system at a rate of 5 l/min. The humidity of the air discharged from the closed system is measured with a hygrometer, from which the amount of steam generated per unit time after the start of heat generation is calculated using equation (1) shown below. The cumulative amount of steam generated for a 10 minute period is taken as the "amount of steam generated". In the formulae below, e represents a water vapor pressure (Pa); es represents a saturated water vapor pressure (Pa, quoted from JIS Z8806); T represents temperature (° C., dry bulb temperature); and s represents a sampling frequency (sec).

Relative humidity $U$ (% $RH$)=($e/es$)×100

Absolute humidity $D$ $(g/m^3)$=(0.794×10$^{-2}$×$e$)/(1+0.00366 $T$)= (0.794×10$^{-2}$×$U$×$es$)/[100×(1+0.00366$T$)]

Unit air volume $P$ (1)=(2.1×$s$)/60

Amount of steam per unit time $A$ $(g)$=($P$×$D$)/1000  (1)

While it is necessary for the mask 1 to raise the skin surface temperature up to a prescribed temperature within a short time, raising the skin surface temperature too high is undesirable for safety. From this point of view, it is preferred to control the heat generation characteristics of the planar heat generator 4 and the steam generation characteristics of the steam generator 3 so that the highest obtainable surface temperature of the skin with the mask 1 on may not exceed 43° C., particularly 42° C.

As is understood from the explanation of the rise time and the duration, one of the features of the mask 1 according to the present embodiment resides in that steam is generated such that the skin surface temperature may rise to a prescribed one in a short time and that that temperature may be maintained for a relatively short time of from several minutes to several tens of minutes. In order to control the rise time and the duration in the above-recited ranges, it is advantageous to control the composition of the planar heat generator 4 and the moisture permeability of the moisture permeable film 5a as described hereunder.

The planar heat generator 4 is to generate heat upon contact with oxygen and thereby to generate steam. The planar heat generator 4 contains a metal, activated carbon, a fibrous material, an electrolyte, and water. The inventors' study has shown that control of the average particle size of activated carbon is advantageous for causing the planar heat generator 4 to generate heat to a high temperature in a short time and to generate a large amount of steam in a short time. Specifically, it is preferred for the activated carbon to have an average particle size of 1 to 100 μm, particularly 5 to 80 μm, for better contact with the metal. The average particle size is measurable by a laser diffraction/scattering method, a light scattering method, a laser diffraction method, a centrifugal sedimentation method, and the like.

The specific surface area of the activated carbon is also important for better contact with the metal. The BET specific surface area of the activated carbon is preferably 300 to 2000 m$^2$/g, more preferably 500 to 1500 m$^2$/g.

The activated carbon in the planar heat generator 4 acts as a reaction accelerator, also serves as a moisture retainer, and also functions as an oxygen retentive supplier for metal. The activated carbon includes coconut shell activated carbon, wood activated carbon, bituminous coal, peat, and lignite. The proportion of the activated carbon in the planar heat generator 4 is preferably 0.5 to 60% by weight, more preferably 1 to 50% by weight, based on the total of the metal, activated carbon and fibrous material of the planar heat generator 4. This range of the activated carbon content produces the following effects. The activated carbon is capable of storing, in the planar heat generator 4, a water content necessary to sustain the oxidation reaction of the metal for keeping the temperature above the human body temperature. The planar heat generator 4 provides sufficient air permeation to secure sufficient oxygen supply and achieve high heat generation efficiency. The heat capacity of the planar heat generator 4 is suppressed with respect to the amount of heat generation, resulting in an enhanced, sufficient increase of temperature that makes a wearer feel her or his face warmed. Furthermore, the activated carbon is prevented from falling off and provides sufficient mechanical strength, such as flexural strength and tensile strength.

The metal used in the planar heat generator 4 is not particularly limited, and any oxidizable metals commonly employed in this type of heat generators can be made use of. The metal preferably has a particulate or fibrous form from the standpoint of handling and molding properties.

Particulate metals include iron powder, aluminum powder, zinc powder, manganese powder, magnesium powder, and calcium powder. Iron powder is preferred because of its handling properties, safety, and production cost. The metal preferably has an average particle size of 0.1 to 300 μm for fixability onto the fibrous material (hereinafter described) and ease of reaction control. It is more preferred to use metal particles of 0.1 to 150 μm in an amount of 50% by weight or more. The average particle size of particulate metal is measured by the same methods as for the activated carbon. Fibrous metals include steel fiber, aluminum fiber, and magnesium fiber. Steel fiber and aluminum fiber are preferred for handling properties, safety, and production cost. The fibrous metal preferably has a fiber length of 0.1 to 50 mm and a thickness of 1 to 1000 μm for molding properties and mechanical strength, surface smoothness and heat generation performance of the resulting sheet.

The proportion of the metal in the planar heat generator 4 is preferably 10 to 95% by weight, more preferably 30 to 80% by weight, based on the total of the metal, activated carbon and fibrous material constituting the planar heat generator 4. This range of the metal content brings about the following effects. The heat generation temperature of the planar heat generator 4 can be increased to or above the temperature that is felt hot to the touch of fingers. Heat generation lasts sufficiently long. Sufficient supply of moisture from activated carbon is secured. The metal hardly falls off. The planar heat generator 4 exhibits sufficient mechanical strength, such as flexural strength and tensile strength. The metal content in the planar heat generator 4 can be determined by ash content measurement in accordance with JIS P8128, vibrating sample magnetization measurement (applicable to iron, of which the magnetization on applying an external magnetic field is made use of), thermogravimetry, etc.

The fibrous material that can be used in the planar heat generator 4 includes any kinds of natural or synthetic fibers with no particular restriction. Natural fibers include plant fibers, such as cotton, kapok, wood pulp, non-wood pulp, peanut protein fiber, corn protein fiber, soy protein fiber, mannan fiber, rubber fiber, hemp, Manila fiber, sisal fiber, New Zealand flax, Luo Buma, coconut, rush, and straw; animal fibers, such as wool, goat hair (including mohair and cashmere), alpaca, angora, camel, vicuna, silk, down, small feather, alginate fiber, chitin fiber, and casein fiber; and mineral fibers, such as asbestos. The synthetic fibers include semi-synthetic ones, such as rayon, viscous rayon, cuprammonium rayon, cellulose diacetate fiber, cellulose triacetate fiber, oxidized acetate fiber, promix fiber, chlorinated rubber, and rubber hydrochloride; and synthetic polymer fibers, such as nylon, aramid, polyvinyl alcohol, polyvinyl chloride, polyvinylidene chloride, polyester (e.g., polyethylene terephthalate), polyacrylonitrile, acrylic polymers, polyethylene, polypropylene, polystyrene, and polyurethane. Metal fibers, carbon fiber, glass fiber, and the like are also useful. Recycled products of these fibers are also employable. Among these fibrous materials preferred are wood pulp, cotton, and polyester in view of their fixing capabilities for the metal and the activated carbon, flexibility and oxygen permeability of the resulting planar heat generator 4, and the cost of production. The average fiber length of the fibrous material is preferably 0.1 to 50 mm, more preferably 0.2 to 20 mm, for securing the strength of the planar heat generator 4 and fiber dispersibility in water.

It is preferred for the fibrous material to have a CSF (Canadian Standard Freeness) of 600 ml or less, more preferably 450 ml or less. With such a freeness, the fibrous material has satisfactory ability to fix and hold the metal, assuring satisfactory heat generation performance of the planar heat generator 4. Furthermore, it is easy to control the breaking length described later within a specific range also described later. As a result, fall-off of the metal from the planar heat generator 4 can be prevented, and the planar heat generator 4 is capable of retaining appropriate mechanical strength. The lower the CSF of the fibrous material, the more preferred. In general, when a planar heat generator is prepared by a papermaking technique using pulp fiber as a sole fibrous material and a small proportion of other components, a CSF less than 100 ml means very poor freeness, which makes de-watering difficult. It can follow that the resulting sheet has thickness unevenness or suffers from molding defects such as burst of blisters upon drying. In the present embodiment, in contrast, since the components other than the fibrous material are present in relatively high proportions, a planar heat generator 4 having satisfactory freeness and a uniform thickness can be obtained. A lower CSF indicates a higher fibril content, and a higher fibril content secures better fixation of the components other than the fibrous material on the fibrous material, which results in high sheet strength. The CSF of a fibrous material can be controlled by adjusting the degree of beating or blending fibers different in CSF.

The proportion of the fibrous material in the planar heat generator 4 is preferably 2 to 50% by weight, more preferably 5 to 40% by weight, based on the total of the metal, activated carbon, and fibrous material constituting the planar heat generator 4. Within this range, fall-off of the metal and the activated carbon can be prevented sufficiently, and the heat generation performance of the planar heat generator 4 can be exhibited sufficiently.

The planar heat generator 4 contains an electrolyte and water in addition to the above-mentioned metal, activated carbon, and fibrous material. In order to secure sufficient steam generation, the contents of the electrolyte and water are preferably such that the planar heat generator 4 contains 5 to 400 parts by weight, particularly 10 to 150 parts by weight, of an aqueous electrolyte solution containing 0.5 to 30% by weight, preferably 1 to 25% by weight, of an electrolyte per 100 parts by weight of total of the metal, activated carbon, and fibrous material. For the same purpose, the electrolyte content in the planar heat generator 4 is preferably 0.02 to 25% by weight, more preferably 0.1 to 15% by weight.

Examples of useful electrolytes include sulfates, carbonates, chlorides, and hydroxides of alkali metals, alkaline earth metals or transition metals. Preferred of them are chlorides of alkali metals, alkaline earth metals or transition metals for their electrical conductivity, chemical stability, and production cost. In particular, sodium chloride, potassium chloride, calcium chloride, magnesium chloride, iron (I) chloride, and iron (II) chloride are more preferred.

If desired, the planar heat generator 4 can contain additives commonly used in papermaking with no particular restriction. Such additives include flocculants, sizes, colorants, strengthening agents, yield improvers, loading materials, thickeners, pH control agents, and bulking agents.

The basis weight of the planar heat generator 4 is preferably 50 to 3000 g/m$^2$, more preferably 100 to 1500 g/m$^2$, still more preferably 150 to 1000 g/m$^2$. Within this range, even in using metal or other components having a large specific gravity, a stable sheet can be formed, and the resulting mask is not too heavy and is comfortable to wear. That is, productivity and convenience of use are satisfactory.

The planar heat generator 4 is not limited by any particular method of making. It is prepared by, for example, first forming a sheet containing the metal, activated carbon, and fibrous material and then adding an aqueous electrolyte solution to the sheet. Addition of an aqueous electrolyte solution to the sheet is desirably conducted in an inert gas atmosphere of nitrogen, argon, etc. Addition of an aqueous electrolyte solution can be carried out by spraying, brush coating, dip coating, gravure coating, reverse coating, doctor blade coating or the like method.

The sheet formation can be carried out by, for example, wet papermaking taught in JP-A-2003-102761 filed by the same Applicant or extrusion with a die coater. Wet papermaking is preferred for production cost and productivity. In other words, the planar heat generator 4 is preferably a sheet formed by papermaking techniques. Papermaking machines useful for wet papermaking include a cylinder paper machine, a foundrinier paper machine, a short-wire paper machine, and a twin-wire paper machine. The slurry used for wet papermaking contains the metal, reaction accelerator, fibrous material, and water and has a solids content preferably of 0.05 to 10% by weight, more preferably of 0.1 to 2% by weight.

The sheet formed by wet papermaking preferably has a breaking length (JIS P8113) of 100 to 4000 m, more preferably 200 to 3000 m, in a dry state for preventing the planar heat generator 4 from breaking or cutting and for obtaining a planar heat generator 4 that is flexible and excellent in heat generation performance. The "breaking length" is obtained as follows. A 15 mm wide and 150 mm long specimen is cut out of a molded sheet in its dry state. The specimen is set on a tensile tester at a gauge length of 100 mm and pulled at a rate of 20 mm/min to measure the tensile strength, from which the breaking length is calculated according to the following equation:

Breaking length $(m)=(1/9\cdot8)\times$tensile strength $(N/m)$ $\times10^6$/specimen's basis weight $(g/m^2)$ The thickness of the molded sheet is preferably 0.08 to 1.2 mm, more preferably 0.1 to 0.6 mm. Within this thickness range, the following advantages are enjoyable. Heat generation performance and mechanical strength of the sheet are secured. The metal, activated carbon, and the like are fixed satisfactorily. A sheet with a uniform thickness and a uniform composition can be prepared in a stable manner. The sheet hardly suffers from damage, such as breakage due to pinhole creation, assuring satisfactory productivity and processability. The sheet has good flexibility so that the mask is easily conformable to the curved contour of the face. The molded sheet (and the planar heat generator 4) may be a combination of strips or pieces arranged in a side-by-side configuration.

The sheet is then impregnated with an aqueous electrolyte solution to obtain a planar heat generator 4. Prior to the impregnation, the sheet can be subjected to craping, slitting, trimming or perforating by needle punching, if desired. By such processing, the sheet will exhibit sufficiently high heat generation performance and steam release performance as desired even though it is thin. Additionally the resulting planar heat generator 4 will have improved flexibility and be more conformable to the contour of the face. In perforating the sheet, the individual perforations preferably have an area of 0.01 to 10 $mm^2$, more preferably 0.1 to 8 $mm^2$, for obtaining sufficient heat generation performance. For the same reason, the density (number) of the perforations is preferably 0.1 to 20, more preferably 1 to 15, per $cm^2$. The shape of the perforations can be a circle, a rectangle, a polygon, an ellipse, an elongated circle, or a combination thereof. Where slits are made through the sheet, the slit length is preferably 1 to 50 mm, more preferably 5 to 30 mm.

In order to obtain desired heat generation performance from a planar heat generator 4 impregnated with an aqueous electrolyte solution, it is preferable to use a stack of the planar heat generators 4. In this case, it is advisable to unite the planar heat generators 4 into an integral body by embossing so as to prevent the planar heat generators 4 from sliding during use of the mask 1. The above-described perforating or slitting is also effective in preventing sliding.

The moisture permeable sheet 5a, which covers one side of the planar heat generator 4, preferably has a moisture permeability (a water vapor transmission rate as specified in JIS Z0208, measured at 40° C. and 90% RH, hereinafter the same) of 500 to 15000 $g/m^2 \cdot 24$ hr, particularly 1000 to 10000 $g/m^2 \cdot 24$ hr. This range is preferred for securing smooth oxygen supply and therefore facilitating rapid heat generation and steam generation. The moisture permeable sheet 5a includes mechanically perforated sheets made of resins, such as polyolefins, e.g., polyethylene and polypropylene, polyesters, polyamides, polyurethanes, polystyrenes, and ethylene-vinyl acetate copolymers; porous sheets prepared by stretching sheets of the above-recited resin containing an inorganic filler to create fine pores by interfacial separation; porous sheets formed by making use of interfacial separation of the crystalline structure of these resins; and porous sheets having interconnecting fine pores formed by foam molding.

For achieving appropriate control of steam generation and temperature, it is preferred for the moisture permeable sheet 5a to have an air permeability (as measured in accordance with JIS P8117, hereinafter the same) of 10000 s/100 ml or less, particularly 5000 s/100 ml or less.

Figure 3:
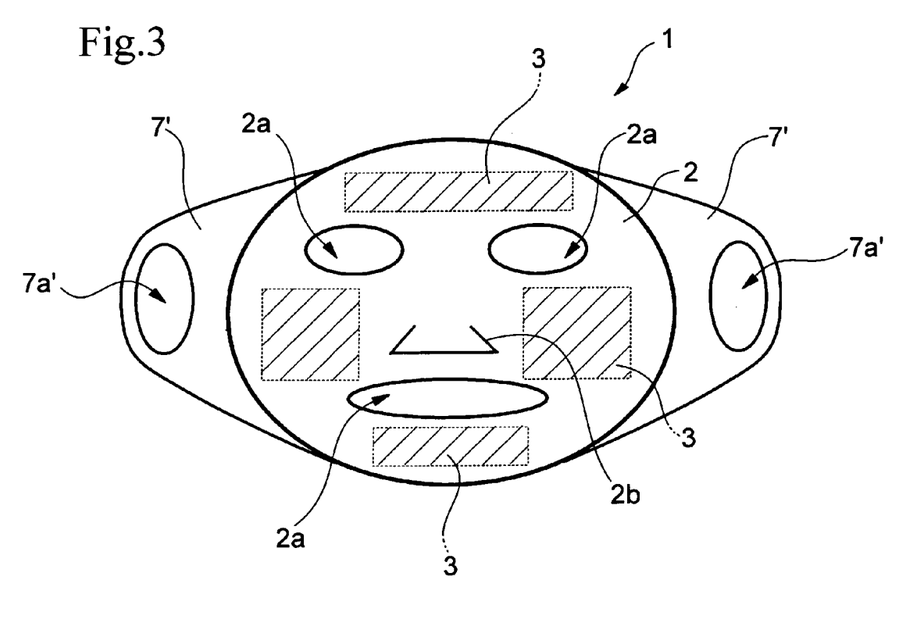
FIG. 3 schematically illustrates a second embodiment of the heat-generative, steam generation facial sheet of the present invention (corresponding to FIG. 1).

A second and a third embodiment of the present invention will then be described with reference to FIGS. 3 and 4. The description with reference to the first embodiment appropriately applies to those particulars of the second and third embodiments that are not described hereunder. The members in FIGS. 3 and 4 that are the same as those in FIGS. 1 and 2 are given the same reference numerals as in FIGS. 1 and 2. The mask 1 of the second embodiment has a pair of fixing flaps 7', 7' extending laterally from the side edges of the mask 1 in place of the fastening straps 7 of the first embodiment. Each flap 7', 7' has a vertically elongated circular opening 7a', 7a' at the end thereof. The openings 7a' are located at positions corresponding to wearer's ears so that the wearer's ears are placed through the openings 7a' when the mask 1 is put on a wearer. In putting the mask 1 on a wearer, the mask body 2 is applied to the face, the flaps 7', 7' are put around the sides of the face, and the ears are put through the respective openings 7a', 7a'. The mask 1 is thus held in place.

The flaps 7' may be of an extensible or non-extensible material. The material of the flaps 7' may be the same or different from that of the mask body 2. The flaps 7' may be integral with the mask body 2 or separately formed pieces that are bonded to the mask body 2 by heat sealing or with an adhesive.

Figure 4A:
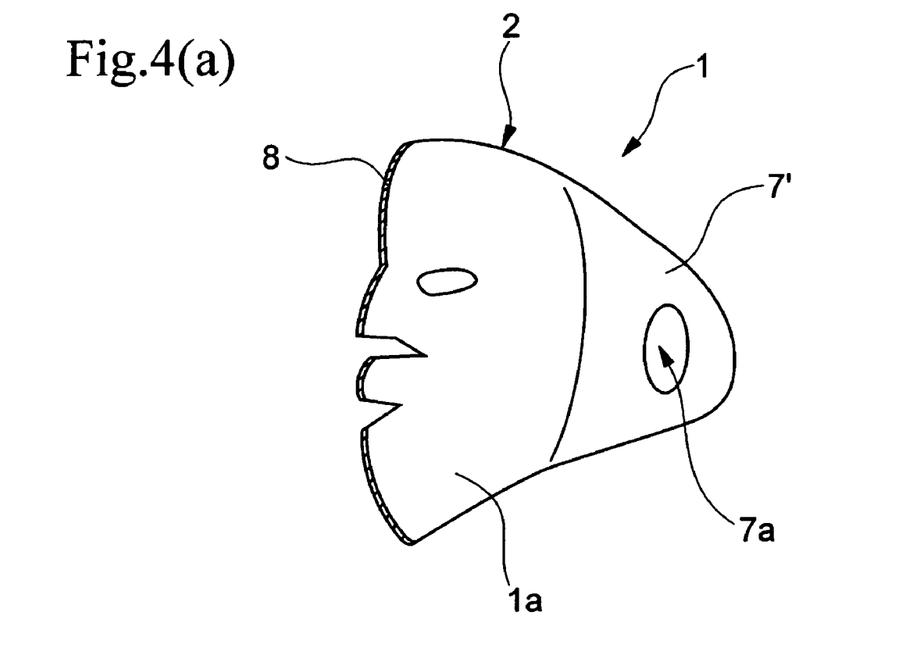
Figure 4B:
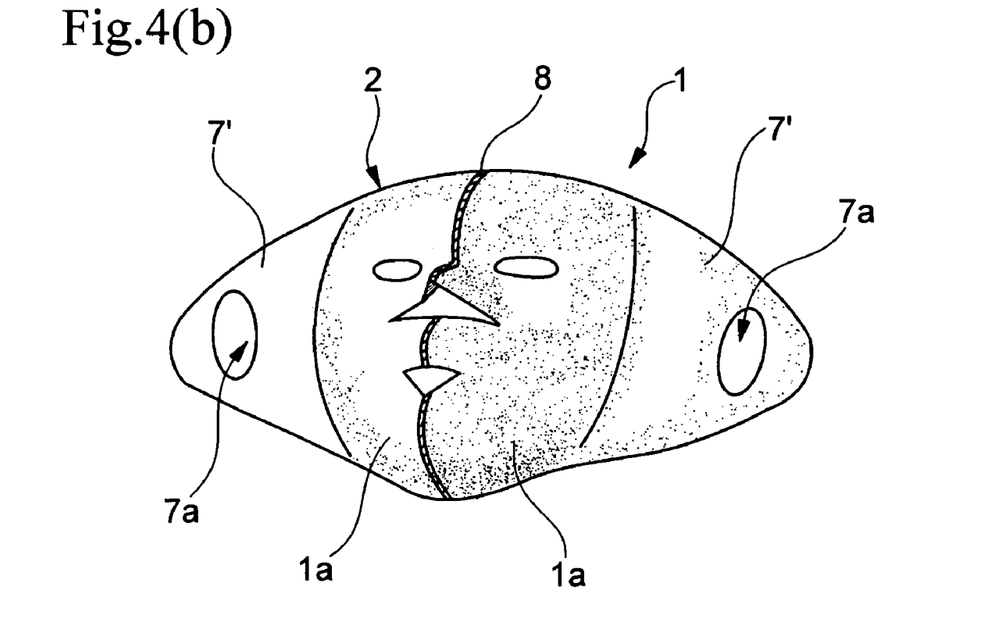
Figure 5:
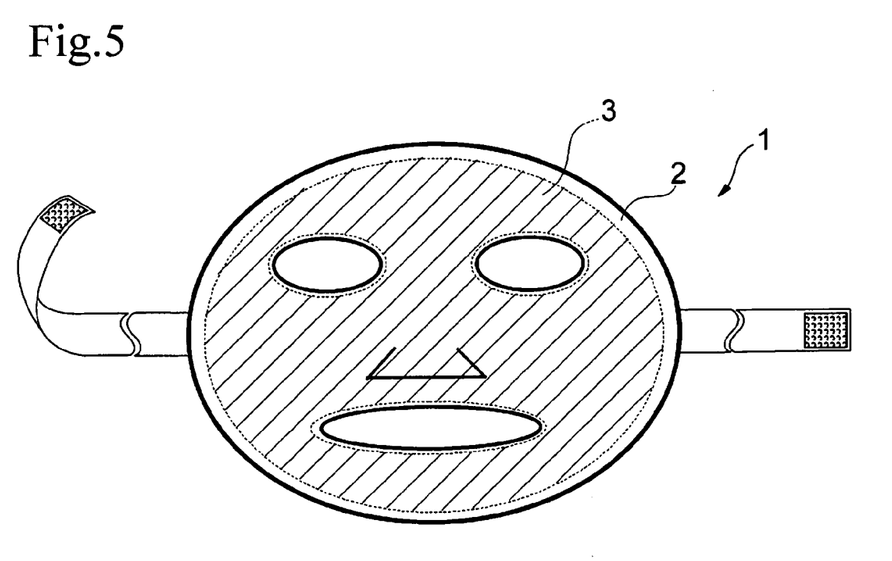
FIG. 5 is a schematic illustration of another embodiment of the heat-generative, steam generation facial sheet of the present invention (corresponding to FIG. 1).

The mask 1 shown in FIG. 4(*a*) and FIG. 4(*b*) according to the third embodiment is designed to have a three-dimensional shape so that it may be brought into more intimate contact with the contour of the face. By this design, the mask 1 is prevented from getting out of position while worn, thereby giving a wearer comfort of use, and is capable of steaming every part of the face uniformly. To make the mask 1 having a three-dimensional shape according to the third embodiment, halves 1a of the mask 1 are prepared and joined together along one of their sides that corresponds to the centerline of a face to form a vertical seal 8 and to complete the mask 1. On unfolding the mask 1 laterally, there is created a three-dimensional shape symmetrical about the vertical seal 8.

While the present invention has been described based on its preferred embodiments, it should be understood that the invention is not construed as being limited to these embodiments. For example, while the mask body 2 of the foregoing embodiments has separately prepared steam generators 3 attached to the skin facing side thereof, the steam generator 3 may be formed to the shape of a face. In this case, the mask body 2 is unnecessary. In this embodiment, the mask is preferably designed to release steam from its entire area in contact with the skin, thereby to produce an enhanced cleansing effect of pore opening. It is also possible that a steam generator 3 having substantially the same shape as the mask body 2 is attached to the skin facing side (inner side) of the mask body 2.

While in the foregoing embodiments the planar holder 5 is made of a moisture permeable film on one side and a hardly moisture permeable film on the other side, both sides of the planar holder 5 may be made of a moisture permeable film. In this case, the planar heat generation from the planar heat generator becomes more uniform.

The design of the mask 1 having a three-dimensional shape is not limited to that of FIG. 4(*a*) and FIG. 4(*b*). For example, the whole mask 1 or the planar heat generator 4 before being attached to the mask body 2 may be shaped on a heat press or a cold press, or the whole mask 1 or the planar heat generator 4 may be bent to have a three-dimensional shape. There is a method in which a plurality of planar heat generators 4 are stuck to make a three-dimensional shape.

The fastening straps 7 which are used as means for fixing the mask 1 to the face in the foregoing embodiments can be replaced with a pair of fastening strings attached to the lateral edges of the mask, the strings being adapted to be tied together behind the head to fix the mask. Otherwise, a tacky gel that is non-irritating to the skin and sticking to the skin may be applied to the skin facing side of the mask, with which the mask can be stuck to the face. Conversely, a tacky gel may be applied to the peripheral portion of the face, and the mask 1 is fixed to the face via the gel. Such a tacky gel includes poly(meth)acrylate, sodium poly(meth)acrylate, alkyl acrylate copolymers, polybutene, natural rubbers, polysaccharides, and modified polysaccharides.

While the mask 1 of the foregoing embodiments has a circular shape the outline of which is in close agreement with the outline of a face, the mask 1 may have other shapes, such as a rectangle, as long as the entire face can be covered.

While the masks 1 according to the above-described embodiments are designed to cover the entire area of a wearer's face, they may be of such sizes that cover only a part of the face, e.g., the forehead and the bridge of the nose (so-called T-zone), undereye areas, cheeks, wings of the nose, eyebrows, and so forth.

As described in detail, the heat-generative, steam generation facial sheet of the present invention is planar and designed to cover the face of a wearer in close contact and is therefore capable of applying steam to the entire facial area at a time. The facial sheet of the invention is also applicable to a desired part of the face. Since it is capable of rising the surface temperature of the facial skin to a desired level in a short time, a wearer can enjoy facial steaming without wait. Since steam generation lasts long enough to open the pores sufficiently, it becomes easier to remove sebum and solidified sebum such as a horny plug and a comedo. The facial sheet of the invention is effective to stimulate blood circulation and maintain a healthy complexion. It also provides relaxation as an additional effect. The heat-generative, steam generation sheet for the face according to the present invention is especially useful for facial cleansing and makeup removal.

What is claimed is:

1. A heat-generative, steam generation facial sheet which is planar and adapted to intimately cover a part or the whole of a wearer's face and has a planar heat generator capable of generating steam upon contact with oxygen,
    said facial sheet generating steam such that the skin surface temperature reaches 34° C. or higher within 120 seconds from contact with air and maintains the skin surface temperature at 34° C. or higher for at least 5 minutes,
    wherein the planar heat generator comprising fibrous material has a Canadian Standard Freeness of approximately 600 ml or less.

2. The heat-generative, steam generation facial sheet according to claim 1, wherein said planar heat generator is a sheet prepared by a papermaking technique and comprises a metal, activated carbon, a fibrous material, an electrolyte, and water, the activated carbon having an average particle size of 1 to 100 μm.

3. The heat-generative, steam generation facial sheet according to claim 2, wherein said planar heat generator contains 10 to 95% by weight of the metal, 0.5 to 60% by weight of the activated carbon, and 2 to 50% by weight of the fibrous material based on the total of the metal, the activated carbon, and the fibrous material and has incorporated therein 5 to 400 parts by weight of an aqueous electrolyte solution containing 0.5 to 30% by weight of the electrolyte per 100 parts by weight of the total of the metal, the activated carbon, and the fibrous material.

4. The heat-generative, steam generation facial sheet according to claim 1, wherein said planar heat generator is hermetically sealed in a planar holder, said planar holder having a moisture permeable film on one side thereof and a hardly moisture permeable film on the other side or having a moisture permeable film on both sides thereof.

5. The heat-generative, steam generation facial sheet according to claim 4, which comprises a sheet body and the heat generator hermetically sealed in the holder,
    said holder being attached to the skin facing side of said sheet body with the moisture permeable film side thereof facing the skin.

6. The heat-generative, steam generation facial sheet according to claim 4, wherein said moisture permeable film has a moisture permeability of 500 to 15000 g/m²·4 hr.

7. The heat-generative, steam generation facial sheet according to claim 1, which comprises a fastening strap extending laterally from each side edge thereof, said fastening straps having attached to the respective free ends thereof an engaging member and a member engageable with the engaging member, respectively, or which comprises a fastening string extending laterally from each side edge thereof.

8. The heat-generative, steam generation facial sheet according to claim 1, which has a fixing flap extending laterally from each side edge thereof, said flap having an opening at the end of the flap to place a wearer's ear there through.

9. The heat-generative, steam generation facial sheet according to claim 1, which has applied to the skin facing side thereof a tacky gel for fixing that is sticky to the skin, or which is adapted to be put on a wearer's face having said tacky gel applied thereto.

10. The heat-generative, steam generation facial sheet according to claim 9, wherein the tacky gel includes at least one of polymethacrylate, sodium polymethacrylate, alkyl acrylate copolymers, a natural rubber, a polysaccharide, or a modified polysaccharide.

11. The heat-generative, steam generation facial sheet according to claim 1, wherein the planar heat generator has a breaking length of approximately 100 m to approximately 4000 m in a dry state.

12. The heat-generative, steam generation facial sheet according to claim 1, wherein the planar heat generator is perforated.

13. The heat-generative, steam generation facial sheet according to claim 1, wherein the planar heat generator is embossed.

* * * * *